United States Patent [19]

Colin et al.

[11] Patent Number: 4,695,432
[45] Date of Patent: Sep. 22, 1987

[54] NITRIDES AND OXYNITRIDES WHICH CAN BE USED AS SELECTIVE DETECTORS OF REDUCING GASES IN THE ATMOSPHERE, AND DETECTION DEVICE CONTAINING THEM

[75] Inventors: Yves Colin, Cesson-Sevigne; Gabriel Rosse, Rennes; Jean Guyader, Agine; Yves Laurent, Cesson-Sevigne, all of France

[73] Assignees: Centre National de la Recherche Scientifique (C.N.R.S.), Paris; Universite de Rennes I, Rennes, both of France

[21] Appl. No.: 845,465

[22] Filed: Mar. 28, 1986

[30] Foreign Application Priority Data

Apr. 2, 1985 [FR] France ................. 85 04989

[51] Int. Cl.$^4$ ............................................. G01N 27/12
[52] U.S. Cl. .................................... 422/98; 73/27 R; 338/34; 436/111; 436/113
[58] Field of Search .................. 73/23, 27 R; 338/34; 324/71.5; 422/94, 98; 423/353; 436/106, 110, 111, 113; 502/200, 525

[56] References Cited

U.S. PATENT DOCUMENTS 3,865,550 2/1975 Bott et al. .
4,197,089 4/1980 Willis et al. .

OTHER PUBLICATIONS

"Variation of the Electrical Resistance of Germanium and Zinc Oxynitride Pellets During Oxygen Adsorption/Desorption", M. Ghers et al, Ann. Chim. Fr., 1985, 10 pp. 113-119.
C. R. Acad. Sc. Paris, t.270, pp. 2052-2055, 6/22/70.
"Preparation and Properties of ZnGeN$_2$", M. Maunaye et al, Mat. Res. Bull., vol. 5, 1970, pp. 793-796.

Primary Examiner—Barry S. Richman
Assistant Examiner—Michael S. Gzybowski
Attorney, Agent, or Firm—Stevens, Davis, Miller & Mosher

[57] ABSTRACT

Nitrides and oxynitrides which can be used as selective detectors of reducing gases in the atmosphere, and a detection device containing them. Selective detectors of nitrogen-containing reducing gases in the atmosphere, in particular ammonia and gases containing NH and/or NH$_2$ groups, of the semiconductor resistance type, the nitrides and oxynitrides according to the invention are of tetrahedral structure and contain:
a metal chosen from the group comprising Li, Na, K, Be, Mg, Ca, Sr, Ba, Zn and Mn;
a second element chosen from the group comprising Si, Ge, P, Al and Ga;
nitrogen and, if appropriate,
oxygen.

5 Claims, 9 Drawing Figures

NITRIDES AND OXYNITRIDES WHICH CAN BE USED AS SELECTIVE DETECTORS OF REDUCING GASES IN THE ATMOSPHERE, AND DETECTION DEVICE CONTAINING THEM

The present invention relates to nitrides and oxynitrides which can be used as selective detectors of nitrogen-containing reducing gases in the atmosphere, in particular ammonia and gases containing NH and/or $NH_2$ groups, and also to selective detection devices containing the said nitrides and oxynitrides.

In the prior art, the majority of gas sensors for which the detection parameter is the electrical resistance of a semiconductor layer use oxides doped to a greater or lesser extent, such as $SnO_2$ or ZnO, which are relatively sensitive to different reducing gases. However, none of them, irrespective of the physicochemical phenomenon on which its operation is based, is particularly selective for nitrogen-containing reducing gases, especially ammonia, to a desirable degree of reliability. All these sensors have mediocre properties of sensitivity, selectivity and precision; moreover, they demand substantial maintenance. It is absolutely impossible to use them effectively as selective sensors of, for example, ammonia.

The object of the present invention was precisely to overcome these disadvantages by considering the use of a large number of other compounds which are stable over a wide temperature range, especially in the presence of ammonia or moisture, and at the same time are capable of adsorbing oxygen so as to favor the detection of nitrogen-containing reducing gases and more specifically ammonia.

According to the present invention, nitrides and oxynitrides of tetrahedral structure will be used as selective detectors of nitrogen-containing reducing gases in the atmosphere, in particular ammonia and gases containing NH and/or $NH_2$ groups, the said nitrides and oxynitrides containing:

a metal chosen from the group comprising Li, Na, K, Be, Mg, Ca, Sr, Ba, Zn and Mn;
a second element chosen from the group comprising Si, Ge, P, Al and Ga;
nitrogen and, if appropriate,
oxygen.

The present invention relates in particular to the use of the nitrides and oxynitrides corresponding to the following general formula as selective detectors of nitrogen-containing reducing gases:

in which:
(i)
$1 < t < 2$
$0 < u < 2$
$0 < v < 2$
$1 < w < 3$
(ii) $2t + 4u = 2v + 3w$
(iii) $(2t + 4u + 6v + 5w)/(t + u + V + W) \geq 4$ The invention relates more particularly to the use of the zinc germanium oxynitrides corresponding to the general formula:

in which:

$1.47 \leq x \leq 1.90$ $0.93 \leq y \leq 1.75$ $1.28 \leq z \leq 1.69$

In view of the fact that these nitrides and oxynitrides are manufactured under ammonia and are physically very stable at normal temperatures, they have the decisive advantage of not reacting directly with ammonia at these temperatures. On the other hand, the atmospheric oxygen which they adsorb by a phenomenon of strong chemisorption reacts reversibly with nitrogen-containing reducing gases, such as ammonia, over a temperature range which depends in particular on the conditions of preparation influencing the stoichiometry of these nitrides and oxynitrides.

These nitrides and oxynitrides can be prepared in a manner known per se, for example by reacting ammonia gas, at temperatures of between 700° and 1000° C., with double oxides of, on the one hand, a metal chosen from the group comprising Li, Na, K, Be, Mg, Ca, Sr, Ba, Zn and Mn, and, on the other hand, an element chosen from the group comprising Si, Ge, P, Al and Ga.

For example, zinc germanium oxynitrides of various stoichiometries have been prepared by reacting a stream of ammonia with coprecipitated and calcined zinc orthogermanate ($Zn_2GeO_4$) at different temperatures and for different times. For the preparation of the nitrides and oxynitrides used within the scope of the present invention, reference may be made for example to C. R. Acad. Sc. Paris, t.270, p.2052-2055 (22nd June 1970) and Mat. Res. Bull. Vol.5, p.793-796 (1970).

These proposed nitrides and oxynitrides have a concentration of valence electrons greater than or equal to 4 and a tetrahedral structure derived from that of wurtzite with half the tetrahedral sites occupied by the cations. Nitrides and oxynitrides of this type are in the form of powders which can be pelletized under pressure or deposited in a thick layer.

The conditions of chemisorption and desorption of oxygen as a function of temperature were determined, as were the conditions of recovery of the initial electrical properties. The temperature range for the optimal reversible reaction of ammonia with absorbed oxygen was fixed. This made it possible to record, at a suitably chosen temperature, a detection of 20 to 2000 ppm of $NH_3$ in an air flow, with a maximum variation of 40 to 50% in the resistance, a response time to an incremental change in $NH_3$ and a recovery time of 1 to 2 minutes.

These nitrides and oxynitrides can therefore be used to advantage for the manufacture of devices for the selective detection, in the atmosphere, of nitrogen-containing reducing gases and in particular ammonia, as well as other gases containing the NH and/or $NH_2$ groups.

According to the present invention, this type of detection device has a semiconductor layer based on one of the abovementioned nitrides or oxynitrides, placed on a support provided with a heating means capable of reaching a temperature of 100° to 250° C., for example, and also a means for measuring the variation in the resistance of the said layer in response to the chemisorption of nitrogen-containing reducing gases on the said layer, the measuring means producing a signal representing the variation in the concentration of the said gases in the vicinity of this layer. Depending on the particular applications envisaged, this signal may be a sound or light signal or alternatively may be displayed as the proportion of nitrogen-containing reducing gases on a graduated scale, for example directly in ppm of ammonia.

Such devices for the selective detection of nitrogen-containing reducing gases in the atmosphere are employed, for example, in refrigerating installations equipped with threshold alarms. In fact, it is appropriate to point out that ammonia accounts for about 70% of the refrigerating fluids used at the present time.

Such detectors are also employed in the dairy industry, the nitric acid and fertilizer industry, canneries, tanneries, animal breeding farms and abattoirs, where offal is incinerated.

Such detection devices are also employed in the nitrogen enrichment of soils by the direct injection of ammonia. The subject of the present invention also makes it possible to monitor silos in which animal feed is complemented with nitrogen, for example by the injection of anhydrous ammonia as the corn enters the silo filler. It should also be stated that, in the agri-foodstuffs sector, ammonia frequently accompanies other atmospheric pollutants. The detection of ammonia therefore makes it possible not only to prevent the appearance of this gas at intolerable or dangerous doses, but also to prevent the appearance of accompanying gases.

Numerous experiments have been carried out to examine the conditions of chemisorption and desorption of oxygen and also the optimal temperature range for the reversible reaction of ammonia with adsorbed results of the experiments carried out on one particular oxygen. To illustrate all these properties, the oxynitride, namely the oxynitride of the formula:

$$Zn_{1.64}GeO_{1.16}N_{1.66}$$

will be indicated below.

The curves representing the results observed are shown in the attached drawings, in which.

The conditions and results of the experiment carried out on $Zn_{1.64}GeO_{1.16}N_{1.66}$ will be explained in greater detail below with reference to the attached figures.

(1) ELECTRICAL CONDUCTIVITY OF $Zn_xGeO_yN_z$ PELLETS IN VACUO (x=1.47 to 1.90; y=0.93 to 1.75; z=1.28 to 1.69)

Figure 1:
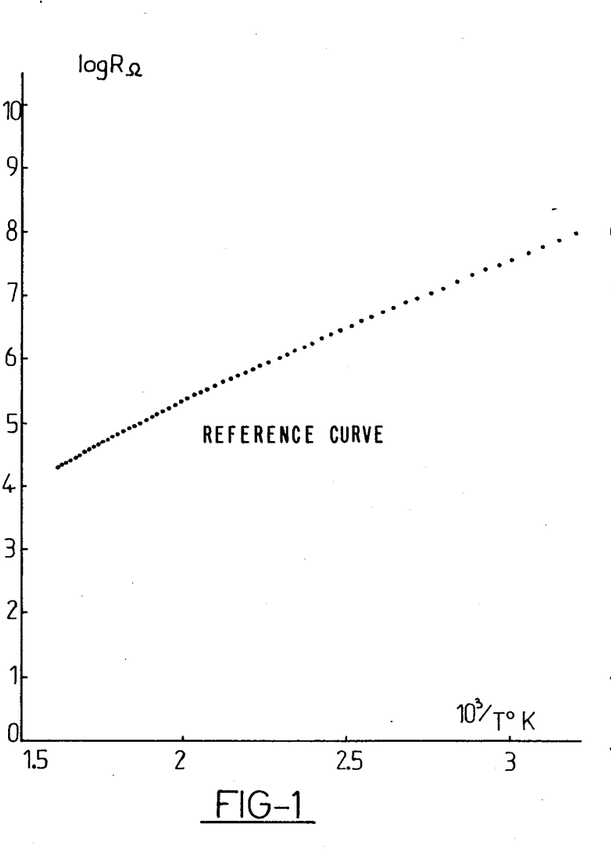
FIG. 1 represents the variations in the electrical resistance R of $Zn_{1.64}GeO_{1.16}N_{1.66}$ pellets as a function of the thermodynamic temperature (reference curve)

7 samples of compressed crystalline powders of various compositions within the limits specified above were tested. As the material readily chemisorbs oxygen, the only reference characteristic as regards electrical conduction is the one obtainable after degassing under a secondary vacuum, at the agreed maximum working temperature imposed. Irrespective of the sample, this characteristic always has the shape of that in FIG. 1, which relates to a sample E of moderate zinc content (x=1.64; y=1.16; z=1.66), showing the resistance R as a function of the thermodynamic temperature T, the sample having been degassed for several hours at 400° C. under a residual pressure of about $10^{-3}$ Pa.

The slope and the mean value of the log of the resistance vary with the composition, an increase in the zinc content causing a decrease in the resistance. It is noted that, in all cases, the value R of the resistance and the value $\alpha$ (negative) of its temperature coefficient are very high, R being of the order of a $M\Omega$ at about 200° C. and $\alpha$ being of the order of $-3.10^5$ $\Omega/K$ at this temperature. It should be observed, however, that these values can be substantially reduced by doping and by heat treatment without thereby impairing the adsorption properties of the samples.

(2) ACTION OF OXYGEN ON THE ELECTRICAL CONDUCTIVITY

(a) Chemisorption

Figure 2:
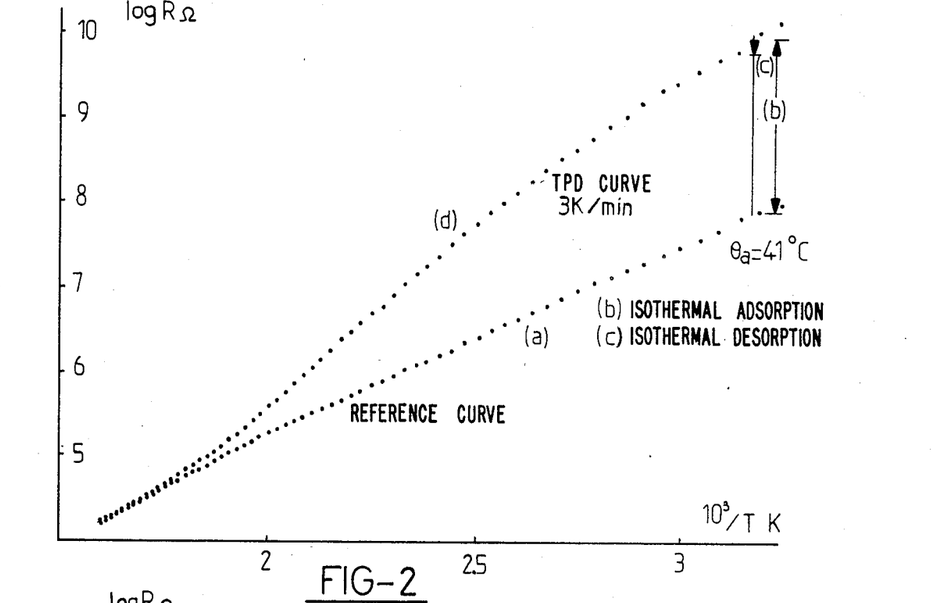
FIGS. 2 to 4 illustrate the changes in the electrical conductivity of this oxynitride due to the effect of the chemisorption of oxygen and programmed desorption, as a function of the thermodynamic temperature.

Numerous experiments proving the reproducibility of the observed phenomena were carried out. FIG. 2, which relates to the same sample E, shows, at $3.2.10^{-3}$ $K^{-1}$ (~39.5° C.), the effect of an isothermal adsorption of oxygen (b) from a point on the reference curve (a): the resistance increases by about two orders of magnitude, showing the strong chemisorption of oxygen; the chemisorbed gas behaves as an electron acceptor and thus lowers the conductivity below the surface of the pellet.

(b) Desorption

In an isothermal desorption, only a very small proportion of adsorbed gas is released (c). A temperature-programmed desorption (TPD) at a rate of 3° K./minute produces curve (d), the shape of which is classical in this field; above 570° K. (297° C.), it becomes identical to reference characteristic (a), demonstrating that all the oxygen is desorbed and the surface of the material has been regenerated.

Figure 3:
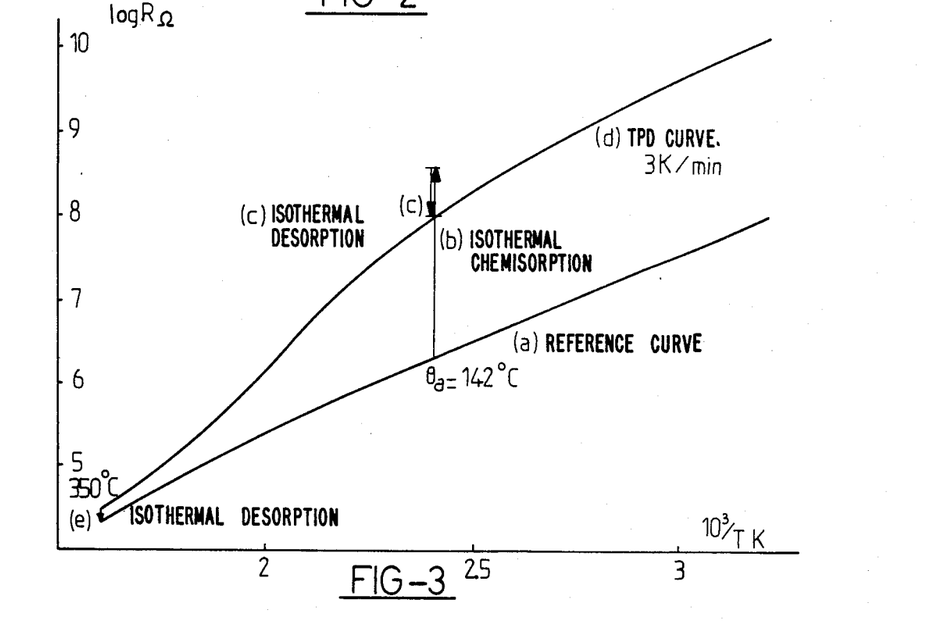
Figure 4:
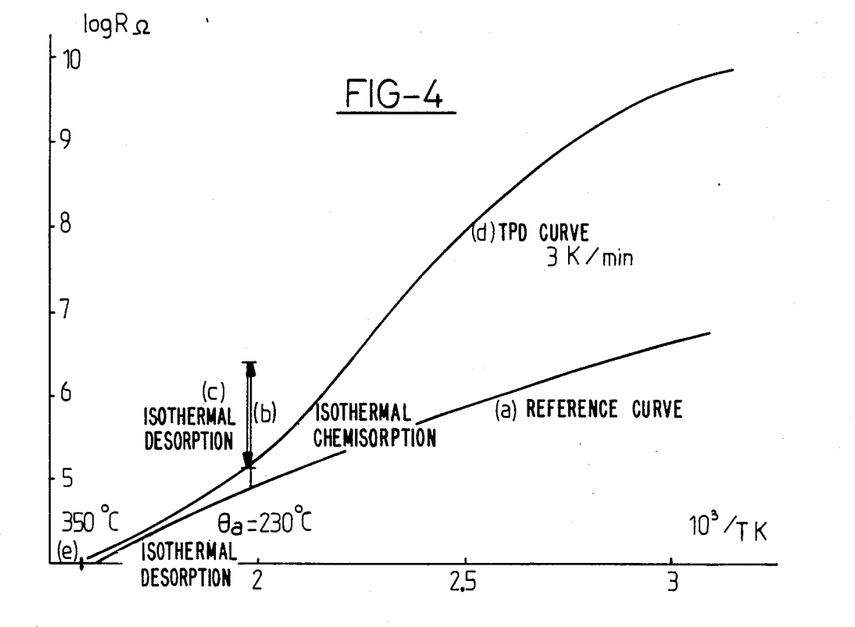

The variation in resistance due to the effect of the chemisorption of oxygen, and the ease of isothermal or temperature-programmed desorption of oxygen, depend on the operating temperature, as shown in the curves of FIGS. 2, 3 and 4. However, reheating in vacuo ($10^{-3}$ Pa) for approximately 30 minutes at 350° C. always restores the surface properties of the sample, the point on the TPD characteristic being brought back to the reference characteristic (arrow e).

(c) Search for an optimal temperature range for the detection of a reducing gas Two groups of quantities are of interest, for a given adsorption/desorption temperature, in the construction of a reducing gas sensor:

the total variation in the resistance obtained under definitive conditions of isothermal adsorption of oxygen, and the corresponding rate of variation, and the total variation in the resistance obtained under definitive conditions of isothermal desorption of oxygen, and the corresponding rate of variation.

The temperature at which the material is used as a sensor of a particular reducing gas will be the result of a compromise to be found between these different quantities.

Figure 5:
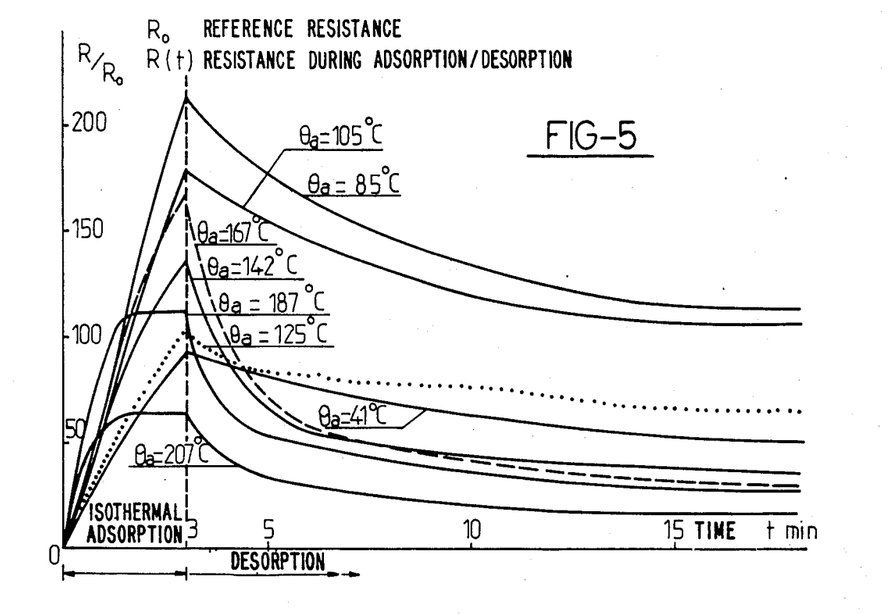
FIG. 5 represents the variations in the electrical conductivity during isothermal adsorptions and desorptions, as a function of the adsorption/desorption temperature $\theta_a$.

It was with this in mind that the oxygen chemisorption/desorption isotherms $R/R_o = f(t)$ were recorded ($R_o$: initial resistance; R: resistance in the presence of adsorbed particles; t: time variable). To prevent oxygen from diffusing into the crystal lattice of the semiconductor grains, the duration $t_a$ of adsorption under atmospheric pressure was limited to 3 minutes, while the duration $t_d$ of desorption leading to a definitive value $R/R_o$ is of the order of 10 to 15 minutes. FIG. 5 shows a few results of these isothermal studies for the reference sample E at various adsorption/desorption temperatures $\theta_a$. It is noted that the adsorption capacity passes through a maximum of about 85° C. The plot of $R_3$ min./$R_o$ as a function of $\theta_a$ (FIG. 6), where $R_3$ min. only represents a saturation value for two values of $\theta_a$, indicates that the adsorption capacity passes through a second maximum at about 170° C. As regards the adsorption rate, it is seen (FIG. 5) that this is slower below 150° C. and a maximum at about 190° C.

Figure 6:
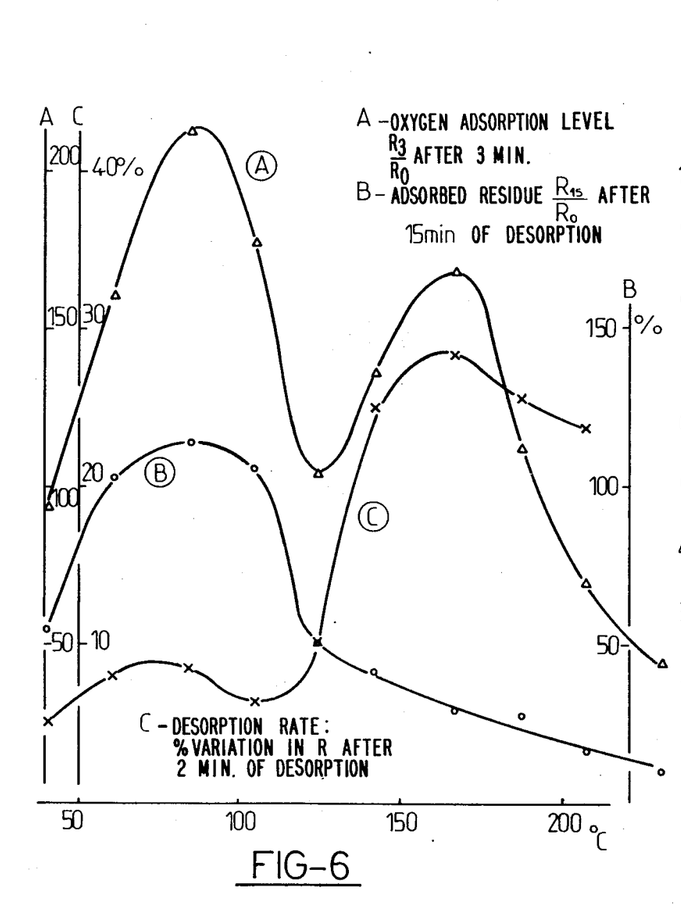
FIG. 6 represents the isothermal desorption of oxygen as a function of the adsorption/desorption temperature $\theta_a$.

As far as the isothermal desorption of oxygen is concerned, FIG. 6, which is deduced from the curves of FIG. 5, shows that this is increasingly efficient above 130° C., but that the desorption rate passes through a maximum at about 170° C.

The most advantageous temperature range for obtaining sensitivity and speed of reaction of a reducing gas with chemisorbed oxygen does indeed appear to be between 150° and 200° C., or in any case above 150° C., for the sample studied. This range depends in general on the deviations from stoichiometry of the material.

(3) ACTION OF AMMONIA GAS ON A $Zn_xGeO_yN_z$ PELLET WHOSE SURFACE IS SATURATED WITH OXYGEN

The oxygen used here is the oxygen from the air, which has been filtered and dried beforehand, In the experimental device used for the tests, the pellet, provided with resistance measuring wires fixed to its surface by a silver lacquer (shown to play no part in the phenomena observed), is placed in an enclosure thermostated between room temperature and 400° C. A circulation of gas (pure or mixed) can be created in this enclosure. The pellet is placed at the point of arrival of the gas whose effects are being studied. The gas flow rates are measured and regulated for the purpose of determining the precise number of ppm of extraneous gas in the air.

Figure 7:
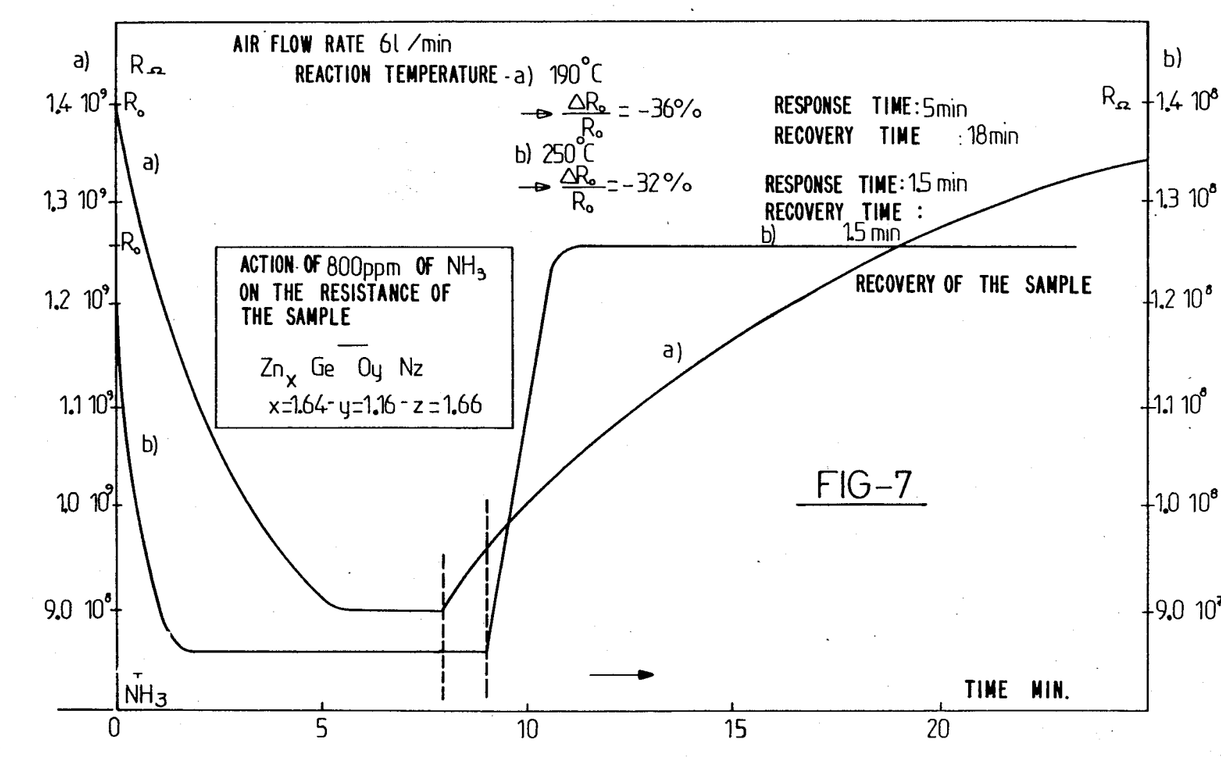
FIG. 7 represents the variations in resistance of this oxynitride following the reaction of $NH_3$ with the chemisorbed oxygen on the surface of the oxynitride.

FIG. 7 gives two examples of the reaction of $NH_3$ with chemisorbed oxygen on the surface of $Zn_xGeO_yN_z$, showing the influence of the working temperature both on the sensitivity of the sensor and on its response time. It should be noted that the response times in FIG. 7b are totally satisfactory for a sensor of this type.

The variation in the response as a function of the proportion of ammonia is essentially linear in the region of low proportions (<1000 ppm). The detection threshold is of the order of 20 ppm. Above 1500 ppm (and depending on the sample), saturation is observed.

In this region, the sample taken as the reference was studied in depth and continued to respond even though it had been operating under all kinds of conditions for several months. If broken, its re-used pieces respond in the same manner.

In the course of these experiments, it was observed that the reaction is more sensitive if the gases arrive at the sample non-thermalized.

(4) ACTION OF OTHER REDUCING GASES UNDER CONDITIONS IDENTICAL TO THOSE USED FOR AMMONIA

Figure 8:
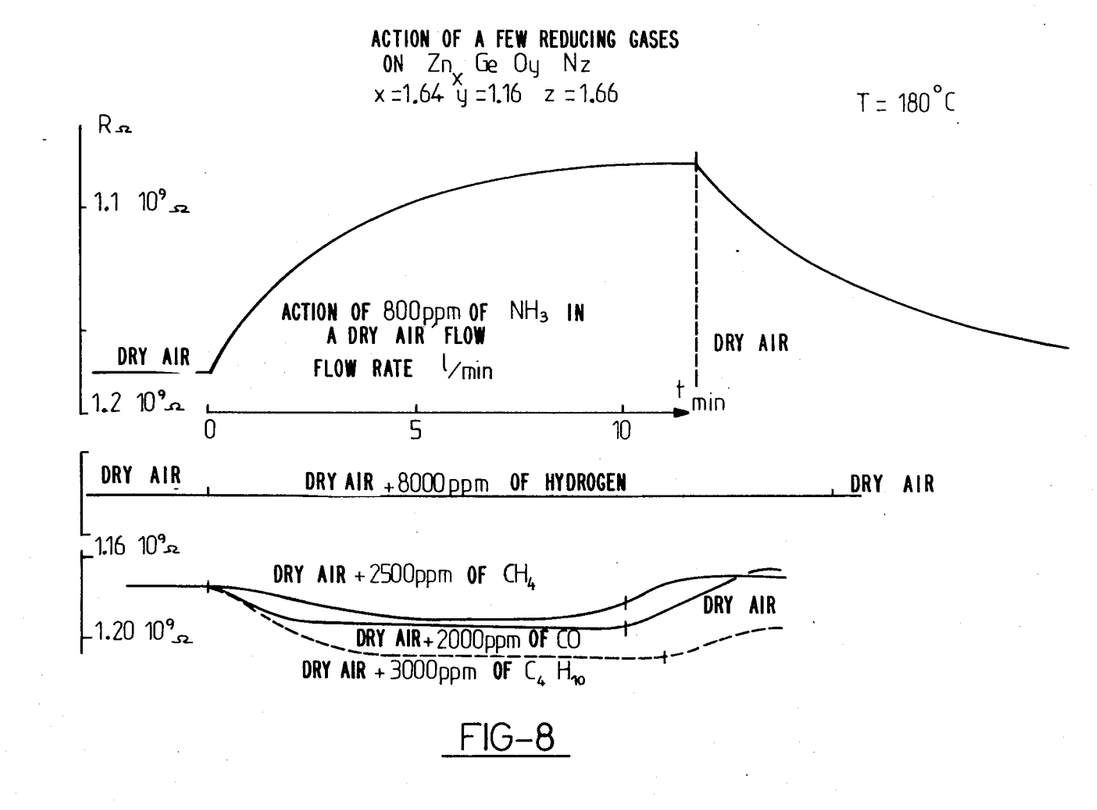
FIG. 8 represents the variations in resistance of the oxynitride due to the action of a few reducing gases.

The effect of air/hydrogen, air/methane, air/carbon monoxide and air/butane mixtures was tested. These components interfering with ammonia, even at a high dose, only produce a slight reaction at the temperatures used, which is moreover in the opposite direction to that of the reaction with ammonia (FIG. 8). After each test, the sensor was regenerated by the passage of filtered dry air, and ammonia again produced its effect; this proves that the interfering components tested did not cause permanent pollution of the detector surface.

(5) ACTION OF MOISTURE

Figure 9:
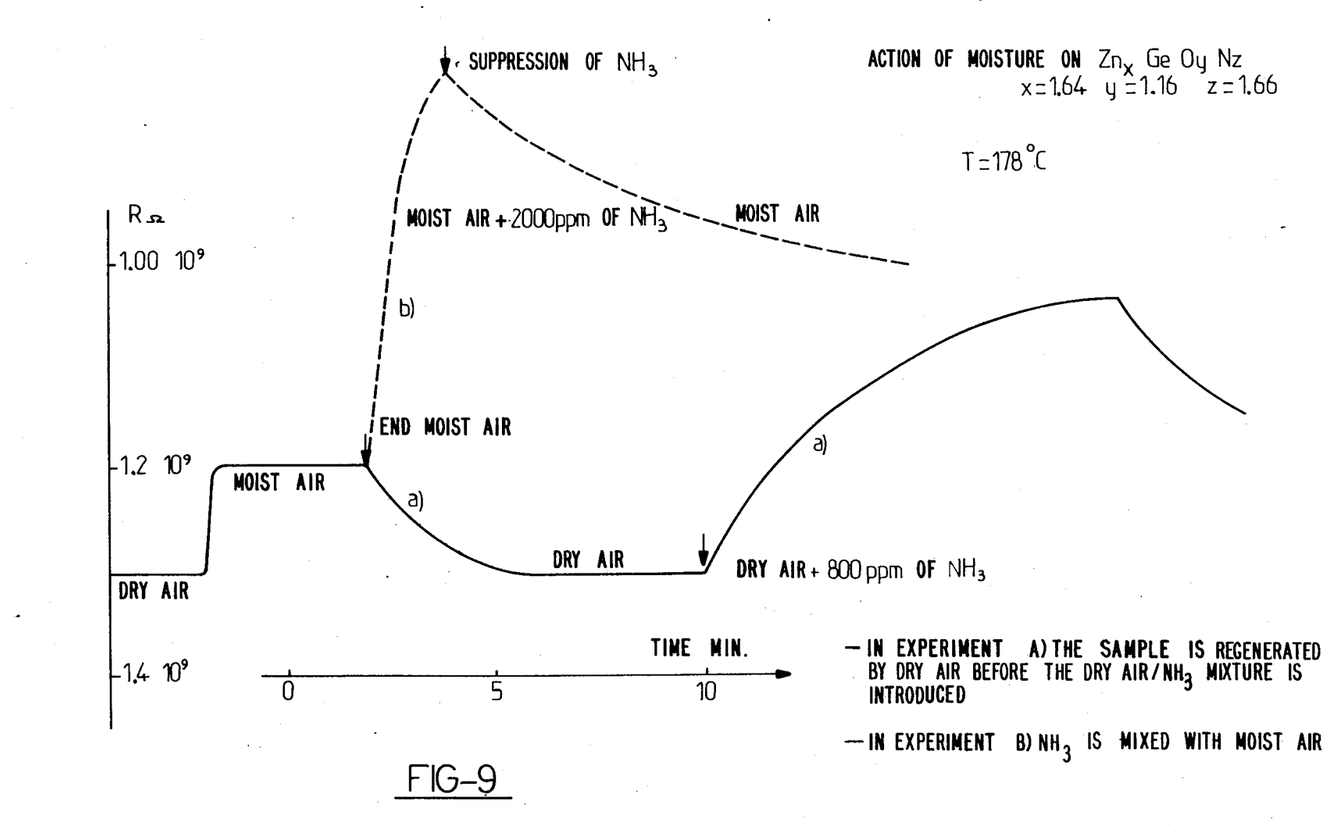
FIG. 9 represents the variations in resistance of this oxynitride in the presence of moisture.

The experiments were conducted under saturated water vapor pressure at 20° C. The results are illustrated by the curves of FIGS. 9a and 9b. These show that the sample is sensitive to moisture in the same direction as to ammonia (FIG. 9) and that the sensitivity to ammonia is considerably increased in the presence of water vapor.

Although this experimental work is solely of an exploratory nature, it is nevertheless evident that:
the response to moisture is immediate,
reversible and
weaker than the response to ammonia.

These results support the observations which it has been possible to make regarding the action of moisture on the behavior of sensors based on ZnO.

All the above results therefore confirm that the nitrides and oxynitrides defined within the scope of the present invention, and in particular zinc germanium oxynitrides, are capable of selectively detecting ammonia.

What is claimed is:

1. A device for the selective detection, in the atmosphere, of nitrogen-containing reducing gases, comprising a support provided with a heating means, said support having a layer thereon of a nitride or oxynitride of tetrahedral structure, and a means for measuring variations in the resistance of said layer in response to chemisorption of nitrogen-containing reducing gases on said layer, said measuring means producing a signal representing the concentration of gases in the vicinity of said layer.

2. The device of claim 1 wherein said layer consists of a nitride which contains a first metal element selected from the group consisting of Li, Na, K, Be, Mg, Ca, Sr, Ba, Zn and Mn; a second element selected from the group consisting of Si, Ge, P, Al and Ga; and nitrogen.

3. The device of claim 1 wherein said layer consists of an oxynitride which contains a first metal element selected from the group consisting of Li, Na, K, Be, Mg, Ca, Sr, Ba, Zn and Mn; a second element selected from the group consisting of Si, Ge, P, Al and Ga; nitrogen and oxygen.

4. The device of claim 1 wherein said nitride or oxynitride is of the general formula $$Zn_t Ge_u O_v N_w$$

in which
 (i)
  $1 \leq t \leq 2$
  $0 < u \leq 2$
  $0 \leq v < 2$
  $1 \leq w \leq 3$
 (ii) $2t + 4u = 2v + 3w$
 and, (iii) $(2t + 4u + 6v + 5w)/(t+u+v+w) \geq 4$.

5. The device of claim 4 wherein said nitride or oxynitride is of the general formula $$Zn_x GeO_y N_z$$

in which
 $1.47 \leq x \leq 1.90$
 $0.93 \leq y \leq 1.75$
 $1.28 \leq z \leq 1.69$

* * * * *